(12) United States Patent
Cewers

(10) Patent No.: US 8,230,857 B2
(45) Date of Patent: Jul. 31, 2012

(54) EXPIRATORY PRESSURE REGULATION IN A VENTILATOR

(75) Inventor: Göran Cewers, Limhamn (SE)

(73) Assignee: RIC Investments, LLC., Wilmington, DE (US)

( * ) Notice: Subject to any disclaimer, the term of this patent is extended or adjusted under 35 U.S.C. 154(b) by 1315 days.

(21) Appl. No.: 11/575,428

(22) PCT Filed: Nov. 9, 2005

(86) PCT No.: PCT/US2005/040736
§ 371 (c)(1),
(2), (4) Date: Oct. 22, 2007

(87) PCT Pub. No.: WO2006/053124
PCT Pub. Date: May 18, 2006

(65) Prior Publication Data
US 2008/0168989 A1    Jul. 17, 2008

(30) Foreign Application Priority Data
Nov. 11, 2004    (SE) .................................. 0402714-0

(51) Int. Cl.
*A61M 16/00* (2006.01)
*A61M 16/20* (2006.01)
(52) U.S. Cl. ......... 128/204.21; 128/204.18; 128/204.22; 128/204.23; 128/205.24; 128/911
(58) Field of Classification Search ............. 128/207.14, 128/207.15, 204.18, 200.26, 200.24, 204.21, 128/207.16, 204.22, 204.23, 204.26, 204.29
See application file for complete search history.

(56) References Cited

U.S. PATENT DOCUMENTS

| | | | | |
|---|---|---|---|---|
| 3,903,881 A | * | 9/1975 | Weigl | 128/204.25 |
| 4,256,101 A | * | 3/1981 | Ellestad | 128/204.23 |
| 4,459,982 A | * | 7/1984 | Fry | 128/204.23 |
| 5,540,220 A | * | 7/1996 | Gropper et al. | 128/204.23 |
| 5,551,419 A | | 9/1996 | Froehlich et al. | |
| 5,918,597 A | * | 7/1999 | Jones et al. | 128/205.18 |
| 6,412,483 B1 | * | 7/2002 | Jones et al. | 128/205.11 |
| 6,564,798 B1 | * | 5/2003 | Jalde | 128/205.24 |
| 6,668,824 B1 | * | 12/2003 | Isaza et al. | 128/202.22 |

* cited by examiner

*Primary Examiner* — Clinton T Ostrup

(57) ABSTRACT

The invention pertains to a ventilator that delivers a flow of gas to an airway of a user, and to communicate a flow of gas from the airway of the user in a controlled manner. The ventilator includes a conduit (1, 3) that carries a flow of gas from the airway of a patient, a first valve (7) coupled to the conduit and adapted to control a pressure or rate of the flow of gas exhausted from the conduit, a first sensor (10) coupled to the conduit and adapted to monitor a pressure of the gas in the conduit, and a controller (12) adapted to control the first valve based on an output of the first sensor. A restrictor (8) is provided in the conduit between the pressure sensor and the patient such that a first volume is defined in the conduit between the first valve and the restrictor and a second volume is defined in the conduit between the patient and the restrictor. The controller controls actuation of the first valve based on a pressure of the first volume monitored by the first sensor.

14 Claims, 3 Drawing Sheets ued States Patent (US 8,230,857 B2)

EXPIRATORY PRESSURE REGULATION IN A VENTILATOR

PRIORITY CLAIM

This application claims priority from Swedish Patent Application Serial No. 0402741-0 filed Nov. 11, 2004.

TECHNICAL FIELD

The present invention pertains to a ventilator adapted to deliver a flow of gas to an airway of a user, and, in particular, to a ventilator with improved pressure control during expiration.

BACKGROUND OF THE INVENTION

It is well known to utilize a dual-limb ventilator or anesthesia machine to deliver a fluid, such as oxygen, air, or other breathing gas or gas mixture, to an airway of patient to augment, supplement, or substitute the patient's own ventilatory effort. For present purposes, the term "ventilator" is used to describe any system or device that delivers a flow of gas or pressurized gas to the airway of a user, alone or in combination with the delivery of other agents, such as anesthesia, supplemental gasses, aerosols, powdered medicaments, or any other material or fluid know to be deliverable to the airway of a patient. Of importance in such situations is the ability to accurately regulate or control the pressure, flow, and/or volume of gas exhausted from to the patient during the expiratory phase of the respiratory cycle.

In a conventional ventilator, the expiratory flow of gas from the patient enters the expiratory limb of the dual-limb circuit. The flow of gas exhausted from the expiratory limb is controlled in a number of ways using an exhaust valve. For example, it is known to use on/off exhaust valve or a proportional exhaust valve in the expiratory limb to control the flow of exhaust gas passing from the ventilator system. Controlling the flow of exhaust gas also controls the pressure in the ventilatory circuit.

In may instances, the exhaust valve is completely shut during inspiration, and completely open during expiration. Providing a relatively unobstructed (open) path during expiration maximizes the patient's comfort during expiration. In some situations, however, there is a need to maintain a certain pressure in the patient's lung at the end expiration. This final pressure may be necessary, for example, to keep the alveoli of the lung expanded so that they do not collapse. This final pressure at the end of expiration is typically referred to as the Positive End Expiratory Pressure (PEEP).

To maintain a certain PEEP, it is known to provide a pressure sensor in the expiratory limb, and regulate the actuation and/or position of the exhaust valve using a controller based on the output of the pressure sensor. In order to obtain a precise control of the expiratory flow/pressure, the controller is configured in a "closed loop" or "feedback" configuration using, for example, a PI or PID control technique as known in the art. By having control over the actuation of the exhaust valve, a ventilator has the ability to regulate the PEEP during expiration. In addition, the exhaust valve can be controlled during other portions of the breathing cycle, even during the inspiratory phase, as may be necessary or desirable depending on the ventilatory mode, pressure levels, or other conditions.

It is well established that it is important that the expiratory resistance is as low as possible, especially when the patient is breathing spontaneously. Therefore, exhaust valves are often made to as to have relatively large dimensions in order to minimize the pressure drop across the exhaust valve. However, larger dimensions for the exhaust valve make it harder to regulate PEEP, which requires controlling very small flow variations. The larger the valve, the harder it is to have a "fine tuned" control over the valve to maintain a precise PEEP level.

Another problem associated with regulation of PEEP in a conventional ventilator is that the control system is attempting to regulate the pressure for a relatively large volume, which has inherent instability. This volume includes the volume of the expiratory limb and the lung volume. The large volumes in combination with resistances and gas masses that have to be transported, leads to delays and instability. For example, the ability to control the pressure deteriorates as a due to the transit time that it takes for a pressure change to effect a large volume of fluid: the greater the volume of fluid, the longer the transmit time. In other words, the large the volume of fluid being controlled by the control system, the slower the system responds to pressure changes. In addition, the patient circuit (tubes) and the patient himself or herself have internal resistances and volumes that affect the ability of a pressure change induced by the valve to take effect in the whole system.

The tubes and the patient's respiratory system also include a certain amount of inherent flexibility, which is referred to as elastance, so that pressure changes cause the volume to expand or contract, thereby changing the volume on the control system. It can be appreciated that changes in the volume as the pressure is increased or decreased by the controller controlling the action of the exhaust valve make it harder for the control system to accurately control that volume to a certain PEEP. In addition, the fluid itself is compressible. This effectively results in low pass filtering of the pressure generation between the valve and the pressure transducer. Thus, the exhaust gas control system has difficultly accurately and quickly controlling the pressure in a stable manner.

A further problem associated with PEEP control that frequently occurs is that the building-up process towards the correct PEEP often includes pressure increases and decreases as the control system attempts to regulate the pressure to the correct PEEP. When the pressure decreases, gas is being removed from the system, if this occurs too rapidly, i.e., is not controlled within a tight tolerance, too much gas may be released and, in the worst case, may lead to alveoli collapse. This is particularly problematic, if the patient is a neonate or a small child with a small lung volume, which is quickly evacuated by a pressure decrease, i.e., by exhausting gas from the system. In other words, if the patient has a small lung volume, the pressure decreases must be tightly controlled, otherwise too much gas may be exhausted from the lungs leading to alveoli collapse.

SUMMARY OF THE INVENTION

Accordingly, it is an object of the present invention to provide a ventilator that overcomes the shortcomings of conventional ventilators. This object is achieved according to one embodiment of the present invention by providing a ventilator that includes a conduit that carries a flow of gas from the airway of a patient, a first valve coupled to the conduit to control a pressure or rate of the flow of gas exhausted from the conduit, a first sensor coupled to the conduit to monitor a pressure of the gas in the conduit, and a controller that controls the first valve based on an output of the first sensor. In addition, a restrictor is provided in the conduit between the pressure sensor and the patient such that a first volume is defined in the conduit between the first valve and the restrictor and a second volume is defined in the conduit between the patient and the restrictor. The controller controls actuation of the first valve based on a pressure of the first volume monitored by the first sensor.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BEST MODE(S) FOR CARRYING OUT THE INVENTION

The present invention will now be described with reference to FIGS. 1 and 3, which illustrates only the expiratory portion of a ventilator according to the principles of the present invention. For example, FIG. 1 omits the inspiratory components of the ventilator, the Y-connector, the patient, or the patient interface that connects the ventilator tubing to the airway of the patient. Instead, this figure focuses on the features of the present invention, which deals with the expiratory components that are connected to the expiratory limb of the ventilator circuit to control the flow of gas from the patient to ambient atmosphere.

Figure 1:
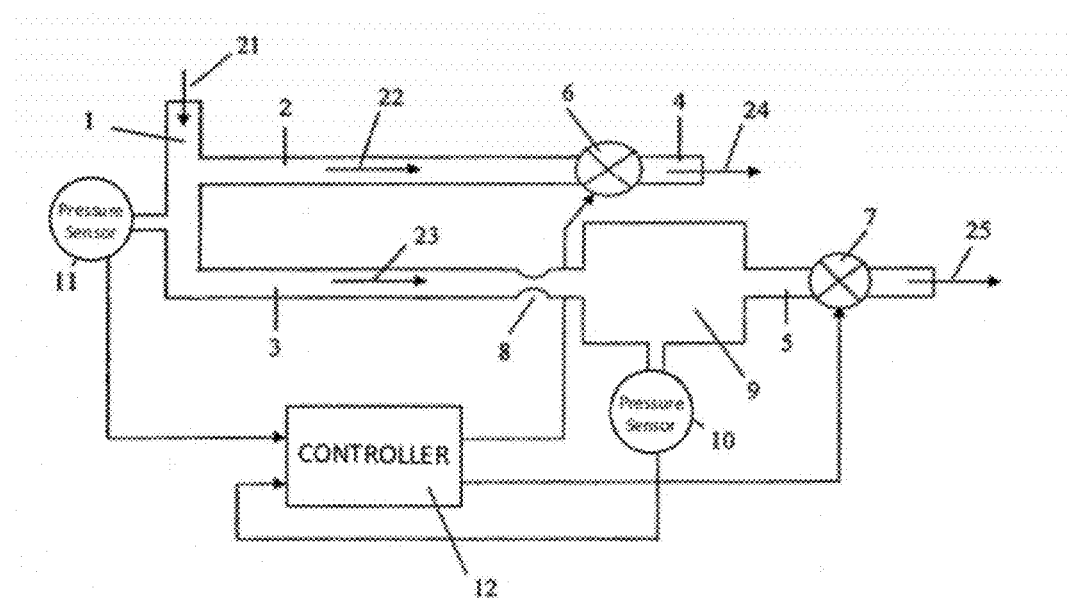
FIG. 1 is a schematic diagram of the expiratory portion of a ventilator according to the principles of the present invention.

As shown in FIG. 1, at least a portion of the expiratory flow 21 of gas from a patient is carried from the patient by a conduit 1, which defines at least a portion of the expiratory limb of the dual-limb ventilator circuit. In the illustrated embodiment, a restrictor 8 provides a flow restriction to a flow of gas 23 in a portion 3 of conduit 1. A chamber 9 is coupled to conduit 1 such that restrictor 8 is disposed between the chamber and the patient. An outlet conduit 5 connected to chamber 9, and a first exhaust valve 7 is provided in the outlet conduit to control the flow of gas 25 exhausted from the system to ambient atmosphere. A first pressure sensor 10 is coupled to the volume of the system downstream of the restructure to measure the pressure in this volume. More specifically, in the illustrated embodiment, first pressure sensor 10 is coupled to chamber 9. The output of first pressure sensor 10 is provided to a controller 12. Controller 12 controls the operation of first exhaust valve 7 based on the output of first pressure sensor 10.

By means of this configuration, a first volume $V_B$ is defined in the conduit between the first valve and the restrictor, and a second volume $V_C$ is defined in the conduit between the patient and the restrictor. The first volume $V_B$ includes the volume in chamber 9 and the volume in the portion of outlet conduit between the chamber and first exhaust valve 7. Firsts pressure sensor 10 measures the pressure of first volume $V_B$. The present invention also contemplates eliminating the additional volume provided by chamber 9 by eliminating the chamber. That is, chamber 9 is optional and can be eliminated so long as a sufficient volume $V_B$ for control purposes exists between restrictor 8 and first exhaust valve 7. Second volume $V_C$ includes the volume in conduit 1, which includes the volume in portion 3 of conduit 1, the volume in the patient's airway and lungs, and the volume in the patient interface device.

Figure 2:
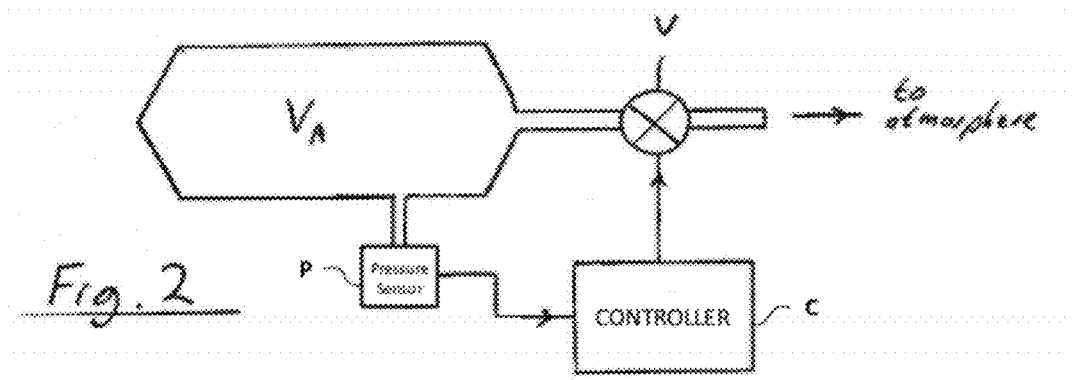
FIG. 2 is a schematic diagram illustrating the control system in the expiratory portion of conventional ventilator.

The present invention also contemplates that first volume $V_B$ can be a variable volume. For example, a piston, collapsible tube, or any other mechanism for selectively changing a volume, can be coupled to volume $V_B$, e.g., by coupling an adjustable volume to conduit 1 between exhaust valve 7 and restrictor 8, so that volume $V_B$ is adjustable and, hence, controllable. This is useful, for example, in situations where it is desirable to maintain a certain ratio between volume $V_B$ and volume $V_C$ In order to perhaps best understand the function of restrictor 8, the pressure/volume/flow control used in the expiratory portion of a conventional ventilation system must first be explained. As shown in FIG. 2, upstream of exhaust valve V there exists a relatively large physical volume, which is represented by volume $V_A$. This volume includes the volume within the conduits that are internal to the ventilator, the flexible patient circuit (expiratory limb) coupled to the external coupling on the ventilator, the patient interface device that communicated the patient circuit with the patient's airway, the airways of the patient, which include the mouth, upper airway, trachea, and lungs. In a conventional ventilator, this relatively large volume $V_A$ is monitored by pressure sensor P. The control system, which includes controller C and valve V attempts to control the system accurately based on this monitored parameter. For example, if the patient is to receive PEEP of 5 cm $H_2O$, the pressure sensor will measure the actual pressure and the controller will adjust exhaust valve V in an attempt to deliver the flow of gas at that target pressure.

However, effective pressure regulation is difficult in this type of arrangement due to the fact that the control system is attempting to regulate a relatively large volume that has inherent instability. For example, the ability to control the pressure deteriorates as a due to the transit time that it takes for a pressure change to effect a large volume of fluid: the greater the volume of fluid, the longer the transmit time. In other words, the large the volume of fluid being controlled by the control system, the slower the system responds to pressure changes. In addition, the patient circuit (tubes) and the patient himself or herself have internal resistances and volumes that affect the ability of a pressure change induced by the valve to take effect in the whole system. The tubes and the patient's respiratory system also include a certain amount of inherent flexibility, which is referred to as elastance, so that pressure changes cause the volume to expand or contract, thereby changing the volume on the control system. It can be appreciated that changes in the volume as the pressure is increased or decreased by the controller make it harder for the control system to accurately control that volume to a certain pressure level. In addition, the fluid itself is compressible. This effectively results in low pass filtering of the pressure generation between the valve and the pressure transducer. Thus, the control system has difficult taking the measurements for pressure transducer P and using these signal to accurately and quickly control the pressure in a stable manner.

Figure 3:
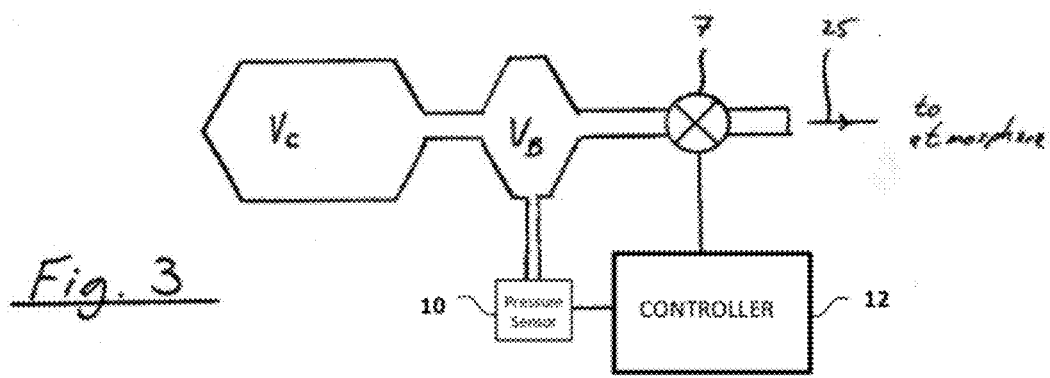
FIG. 3 is a schematic diagram illustrating the control system in the expiratory portion of a ventilator according to the principles of the present invention.

Restrictor 8, in essence, separates volume $V_A$ into two smaller volumes $V_B$ and $V_C$, as illustrated in FIG. 3. Pressure sensor 10 is arranged so as to measure the pressure of the smaller volume, which is closer in proximity to first exhaust valve 7 volume $V_B$, and the control system (including controller 12 and first exhaust valve 7) is arranged to control the pressure of smaller volume $V_B$. In an exemplary embodiment of the present invention, volume $V_C$ is at least two times that of $V_B$. However, the present invention contemplates that volume $V_C$ can be ten times that of $V_B$ or more.

The control system controls the pressure of volume $V_B$. Because this is a relatively small volume, with less inherent instability, e.g., less resistance to flow, less internal elastance, less gas mass to accelerate, and a relatively small volume of fluid contained therein, the control system is better able to accurately and quickly control the pressure of volume $V_B$, and in a much more stable fashion, than that of volume $V_A$. Thus, restrictor 8 partly isolates the pressure control loop from the large volumes to make it easier for the control system to control the pressure of the smaller volume accurately.

There is a fluid communication between volumes $V_B$ and $V_C$ through the restrictor. Thus, pressure control that is done with respect to volume $V_B$ is translated into volume $V_C$, albeit with a slight lag or delay. However, those skilled in the art can appreciated that the size of the restriction can be selected so as to minimize this delay will still providing a useful amount of separation between volumes $V_B$ and $V_C$ so that the control system functions with the desired degree of precision. It should also be noted that restrictor 8 is also configured such that the gas flow through the restriction is sufficient to provide an adequate control of the pressure experienced by the patient.

It should be further noted that providing an intentional restriction in the expiratory limb of a ventilator is counterintuitive to the proper function of a conventional ventilator. Using conventional wisdom, the flow of gas existing the patient should have as little resistance as possible, at least until the PEEP level is reached, so that the patient can comfortably exhale again a minimal amount of pressure drop.

In an exemplary embodiment of the present invention, restrictor 8 is configured to have a pre-determined pressure-flow curve. This curve may have any one of a variety of configurations, for example linear or non-linear. A variety of configurations for restrictor 8 are contemplated by the present invention to provide the desired pressure-flow curve. For example, the restrictor may take the form of a fixed element, such as a net, mesh, screen, aerodynamically shaped element or elements, disposed in the flow path of conduit 1. The restrictor may also include one or more movable elements, such as flaps, slats, vanes, that alter the opening or geometry of the restrictor with changes in the pressure or flow to which the restrictor is subject. The present invention further contemplates that restrictor 8 can be removably disposed in conduit 1 so that different sizes, shapes, or configurations of restrictors can be chosen for different patient categories. This also allows for ease of cleaning of the restrictor.

Moreover, the restrictor can be configured so as to have an adjustable flow restriction, so that the degree of flow restriction can be controlled either manually or automatically. For example the present invention contemplates that controller 12 may adjust the amount restriction provided by restrictor 8 based on the monitored conditions of the system and/or patient, so that a suitable degree of restriction is provided that strikes a balance between the objectives noted above are achieved.

In a further exemplary embodiment, the resistance to flow provided by restrictor 8 is variable so that the amount of fluid communication between volumes $V_B$ and $V_C$ can be dynamically adjusted, e.g., for low minute volumes, the restriction is adjusted to a maximum value, so that the control of the pressure in volume $V_C$ is as fast as possible. This is particularly advantageous in the ventilation of children or neonates, in which case it should be possible to control small minute volumes with high accuracy and with quickness of the pressure control. Likewise, where large minute volumes are needed, the restriction may also be released, such that still a restriction is present, but in such a way that higher instantaneous flows may be generated by the expiratory portion of the ventilator for a given pressure differential. As noted above the variable choking function of the restrictor may be implemented in different ways, e.g., elements such as nets or aerodynamically shaped elements, can be moveably inserted into the flow channel In an exemplary embodiment of the present invention, controller 12 is a PID controller, so that the pressure in the chamber, which is monitored by pressure sensor 10, is maintained at a predetermined pressure, e.g. a desired PEEP level. Of course the present invention contemplates that the pressure in volume $V_B$ can be controlled in any way, for example to follow a predetermined profile during the inspiratory or the expiratory phase of the respiratory cycle.

Figure 4:
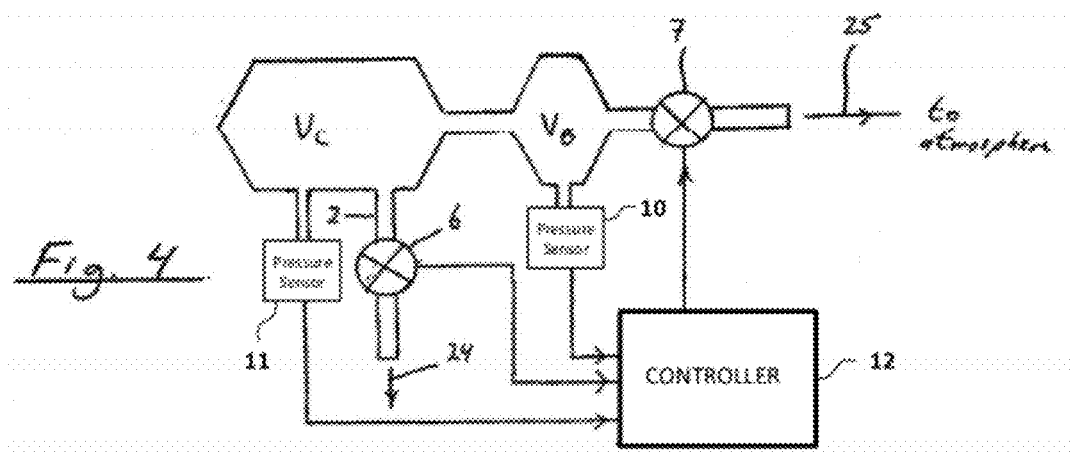
FIG. 4 is schematic diagram illustrating the control system in another embodiment of the expiratory portion of a ventilator according to the principles of the present invention.

Referring again to FIG. 1, the present invention contemplates providing a second conduit 2 to provide a second exhaust gas flow 22 from the patient to ambient atmosphere. A second exhaust valve 6 is provided in conduit 2 to control a flow of exhaust gas 24 to ambient atmosphere. In the illustrated embodiment, second exhaust valve 6 operates under the control of controller 12. An optional conduit 4 is coupled to the outlet of second exhaust valve 6. In essence, as shown in FIG. 4, this second exhaust flow path provides a direct coupling of volume $V_C$ to ambient atmosphere, i.e., without a flow restriction.

The purpose of the this secondary pathway for the flow of exhaust gas is to provide a gas flow path having a minimal resistance during expiration. Thus, conduit 2 and second exhaust valve 6 are configured and arranged to provide a minimal pressure drop from the patient to the ambient atmosphere.

When no PEEP control is need, the present invention contemplates that first exhaust valve 7 is kept closed, and the pressure in the expiratory portion of the ventilator circuit $V_C$ is controlled by actuating second exhaust valve 6. If, however, PEEP is desired, second exhaust valve 6 can be used to provide a "macro" control over the pressure in volume $V_C$, and the first exhaust valve 7 can be used to provide "micro" control over the pressure in volume $V_C$ by means of controlling the pressure in volume $V_B$, which is easier to control for the reasons noted above.

During expiration with PEEP, second exhaust valve 6 may first be opened, so that the pressure in volume $V_C$ quickly moves toward the desired PEEP level. The present invention contemplates providing a second pressure sensor 11 that monitors the pressure in the expiratory portion of the ventilator circuit $V_C$. Second exhaust valve 6 can be controlled by controller 12 based on the output of second pressure sensor 11. When the patient pressure approaches the desired PEEP level, second exhaust valve 6 is closed and the PEEP control is taken over by first exhaust valve 7 based on an output of pressure sensor 10 as the controlled variable.

It should again be noted that the present invention contemplates that restrictor 8 is a variable restrictor. If this is the case, and if restructure has a sufficiently large dynamical range of variable restriction, the second exhaust flow path that includes second exhaust valve 6 may be eliminated. For example, the present invention contemplates that the expiration resistance attained with the variable restriction be comparable to that achieved by placing second exhaust valve 6 in the fully open position. A variable flow restriction implies also an advantage for different patient categories, because a large patient with large expiration flow requires a smaller restriction than a child in order for both patients to experience a breathing resistance during expiration.

It should also be noted that the pressure drop occurring across restrictor 8 may be used as a measure the rate of gas flow 23. That is, restrictor 8 may be formed as part of a flow sensor.

Figure 5:
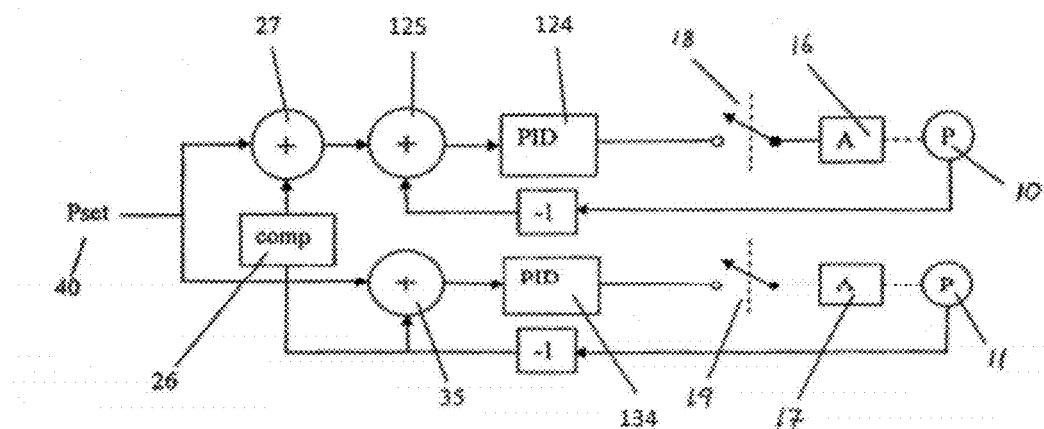
FIG. 5 is a schematic diagram of the control system used to control the expiratory portion of the ventilator shown in FIG. 1.

An exemplary embodiment of a PID controller 12 will now be described with reference to FIG. 5. Pressure in volume $V_B$ is measured by pressure sensor 10 and pressure in volume $V_C$ is measured by pressure sensor 11. Switches 18 and 19 control to valve actuators 16 and 17, which control the actuation of first exhaust valve 6 and second exhaust valve 7, respectively. A switched off valve control implies, in this embodiment, that the valve is closed. That is, when switch 18 or 19 is open (off), valve 6 or 7, respectively, is closed.

When switch 19 is closed, valve actuator 17 causes second exhaust valve 6 to close, thereby causing a pressure increase in the expiratory limb 21, volume VC, which is sensed by pressure sensor 11. The output of pressure sensor 11 is provided to adder 35, where it is subtracted from a set-point pressure Pset 40, which is the set PEEP pressure, for example. The output of adder 35 is provided to a PID controller 134. By means of this control loop, the pressure in volume VC may quickly be controlled to a desired pressure, albeit with limited accuracy and stability.

When the pressure in volume VC reaches or gets close to a desired pressure, actuator 17 is disconnected by switching off switch 19. At the same time, switch 18 connects a second control loop, which comprises actuator 16 (second exhaust valve 7), pressure sensor 10, and adder 125 via PID controller 124, for controlling the pressure in volume VB. This control loop works in the same way as the one described above, with the difference being that the set-point pressure Pset 40 is compensated in compensation block 26 with signals from the patient pressure sensor 11.

However, this control loop will be more stable, because it primarily works to control the pressure in a smaller volume $V_B$, as opposed to $V_C$ or $V_A$, due to the presence of restrictor 8. In this way, a stable pressure regulation is achieved, while the regulator simultaneously fine tunes the pressure towards a desired patient pressure by means of compensation block 26. Compensation block 26 adjusts the set value provided to adder 27, especially when there is a flow 23 through restriction 8. Flow 23 is dynamically created during the pressure control process, and can even have a constant component if the ventilator has a bypass flow during the expiration.

Figure 6:
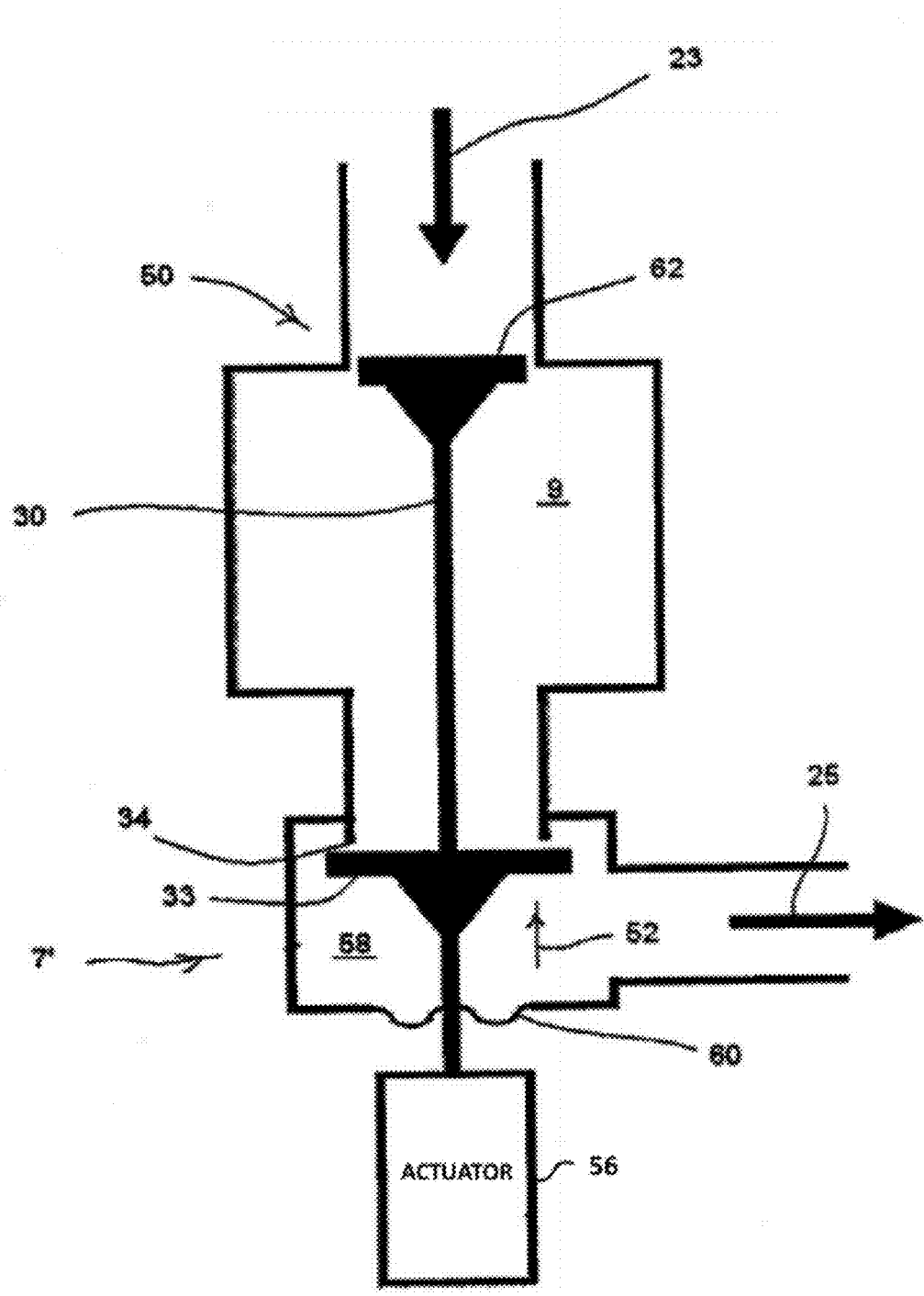
FIG. 6 is a schematic diagram of a technique for controlling a degree of restriction provided in the expiratory portion of a ventilator according to the principles of the present invention.

As noted above, the present invention contemplates that restrictor 8 can be a variable restrictor, i.e., the geometry and/or degree of restriction provided by the restrictor can be controlled or changed. FIG. 6 schematically illustrates an example of a variable restrictor 50 in which the degree of restriction provided by the variable restrictor is controlled based on the actuation of first exhaust valve 7'. More specifically, variable restrictor is mechanically coupled to first exhaust valve 7' so that changes in the position of the first exhaust valve result in changes in the size and/or geometry of the expiratory flow restriction.

In this embodiment, first exhaust valve 7' includes a plate 33 that is capable of moving toward a valve seat 34, as indicated by arrow 52. The mechanical coupling consists of a shaft 30 that is moved via an actuator 56, which is also used to move plate 33 to control the degree of opening of first exhaust valve 7'. Actuator 56 is isolated from the gas outlet in a valve chamber 58 by a membrane 60.

As actuator 56 moves shaft 30 when controlling first exhaust valve 7', a restrictor body 62 in variable restrictor 50 also moves due to the mechanical coupling between plate 33 and restrictor body 62 via shaft 30. In this manner, a variable flow restriction in gas flow path 23 is provided upstream of volume 9. In the case when a big exhalation flow with a minimal resistance to the exhalation flow is needed, actuator 56 opens first exhaust valve 7' by moving plate 33 away from valve seat 34. This also causes a decrease in the size of the flow restriction imposed by variable restrictor 50 due to movement of restrictor body 62 via shaft 30 toward chamber 9, causing little or no flow restriction in the expiratory limb of the patient circuit, and, hence, a minimal exhalation flow resistance.

The present invention contemplates that the ventilator of the present invention can include devices, components, software, communication links, etc., typically associated with ventilators. Examples of devices typically used with a ventilator include humidifiers, nebulizers, filters, etc. For example, bacteria and other filters are typically provided in the expiratory flow path to prevent materials exhausted by the patient or not used by the patient, such as anesthesia, from entering the ambient atmosphere.

Although not shown, a user interface device can be provided to allow a user to manually set up and/or control the ventilator. This interface can be provided directly on the ventilator in the form of a keypad, touchscreen, knob, dials, etc., or it can be remote therefrom with a hardwired or wireless communication link being used to communicate the remote device with the ventilator to set up and/or control the ventilator.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A ventilator adapted to deliver a flow of gas to an airway of a user, and to communicate a flow of gas from the airway of the user in a controlled manner, the ventilator comprising: a conduit that is configured to carry a flow of gas from the airway of the user, a first valve operatively coupled to the conduit and adapted to control a pressure or rate of the flow of gas exhausted from the conduit, a first pressure sensor operatively coupled to the conduit and adapted to monitor a pressure of the gas in the conduit, a controller adapted to control the first valve based on an output of the first sensor, and a restrictor in the conduit, wherein the restrictor is configured to be placed between the first pressure sensor and the user, the restrictor being configured to restrict a flow of gas from the user to the first valve, wherein the restrictor is configured to define a first volume of gas in the conduit between the first valve and the restrictor and a second volume of gas in the conduit between the user and the restrictor, and wherein the controller controls actuation of the first pressure valve based on a pressure of the first volume monitored by the first pressure sensor.

2. The ventilator of claim 1, wherein the restrictor has a fixed geometry.

3. The ventilator of claim 1, wherein the restrictor is configured to provide a linear pressure/flow relationship.

4. The ventilator of claim 1, wherein the restrictor has an adjustable degree of restriction, and wherein the controller controls the degree of restriction provided by the restrictor.

5. The ventilator of claim 1, further comprising a chamber operatively coupled to the first conduit between the restrictor and the first valve such that the chamber defines at least a portion of the first volume.

6. The ventilator of claim 5, wherein the first pressure sensor is operatively coupled to the chamber so as to measure a pressure of gas in the chamber.

7. The ventilator of claim 1, further comprising a second pressure sensor operatively coupled to the first conduit between the restrictor and the user, wherein the first valve is further controlled by the controller based on an output of the second pressure sensor.

8. The ventilator of claim 1, further comprising a second valve operatively coupled to the first conduit between the restrictor and the user, wherein the second valve is controlled by the controller.

9. The ventilator of claim 8, further comprising a second conduit that couples the second valve to the first conduit.

10. The ventilator of claim 8, further comprising a second pressure sensor operatively coupled to the first conduit between the restrictor and the user, wherein at least one of the first valve and the second valve are controlled by the controller based on an output of at least one of the first sensor and the second sensor.

11. The ventilator of claim 8, wherein a pressure drop across the second valve is less than a pressure drop across the restrictor and the first valve.

12. The ventilator of claim 1, further comprising a mechanical coupling between the first valve and the restrictor such that at least one of a size and a geometry of a restriction provided by restrictor changes based on actuation of the first valve.

13. The ventilator of claim 1, wherein the restrictor has a variable geometry and wherein an amount of restriction provided by the restrictor is controlled by the controller.

14. The ventilator of claim 1, wherein the restrictor is configured to provide a non-linear pressure/flow relationship.

* * * * *